United States Patent [19]

Ostermeyer

[11] Patent Number: 5,265,940
[45] Date of Patent: Nov. 30, 1993

[54] FLEXIBLE BOWL TIP TRUCK

[76] Inventor: Bernd Ostermeyer, Lot 6, Pheasant Drive, McMinns Lagoon, Darwin N.T. 5790, Australia

[21] Appl. No.: 656,071
[22] PCT Filed: Jun. 27, 1990
[86] PCT No.: PCT/AU90/00274
  § 371 Date: May 28, 1991
  § 102(e) Date: May 28, 1991
[87] PCT Pub. No.: WO91/00195
  PCT Pub. Date: Jan. 10, 1991

[30] Foreign Application Priority Data

Jun. 29, 1989 [AU] Australia ............... PJ 4988
Jul. 4, 1989 [AU] Australia ............... PJ 4071

[51] Int. Cl.⁵ .............................. B60P 1/28
[52] U.S. Cl. ........................ 298/1 B; 298/18
[58] Field of Search ............ 298/2, 1 B, 18; 296/184, 39.2

[56] References Cited

U.S. PATENT DOCUMENTS 4,494,798  1/1985  Bailey .................. 298/22 P

FOREIGN PATENT DOCUMENTS 816057    7/1949  Fed. Rep. of Germany ....... 298/18
1209761   3/1960  France .
2331462  10/1977  France ................... 298/1 B
WO89/02838 4/1989 PCT Int'l Appl. .
166579    2/1965  U.S.S.R. .
1449394   1/1989  U.S.S.R. .

OTHER PUBLICATIONS

"Rubber floored body ...", Geoff Mead, *Construction Plant & Equipment*, May 1985, pp. 19-20.

Primary Examiner—Michael S. Huppert
Assistant Examiner—Gregory A. Morse
Attorney, Agent, or Firm—Kinney & Lange

[57] ABSTRACT

A tipping system for use in a vehicle including a container having an upper perimetrical frame with an open top and a bowl made of flexible material is suspended from the frame and including means to interact with the bowl in the discharge position to control the shape of the bowl so that contents carried therein will gravity discharge over one side of the perimetrical frame, is disclosed.

16 Claims, 6 Drawing Sheets

FLEXIBLE BOWL TIP TRUCK

BACKGROUND OF THE INVENTION

The present invention relates to tipping systems. Particularly but not exclusively, it relates to a tipping system incorporated in a vehicle and wherein side tipping is involved such as in a doorless side tipper vehicle. Doorless side tipping has been proposed to be provided in road and rail trucks, trailers and semi-trailers for bulk or mass material haulage and transport.

In International patent application WO89/02838 a side tipper support system for a side tipping bulk transport vehicle has been disclosed. The container body has a hinge at one side providing a low pivot point and hydraulic rams positioning on the other side. The rams are two stage, the first stage being single acting and the second stage being double acting with a balancing over ccentre valve. The body in the transport or non-tipped position is supported on feet so that the hinge and rams do not support the load. Further, the body is inwardly inclined on the tipping side to reduce the extent of tipping movement required to discharge the contents of the body.

The problems with the currently known constructions of side tipping bodies are that if the body is of the conventional generally rectangular cross-section, it is either necessary to provide doors on the dicharge side of the body, which are opened when the body is tipped, or it is necessary for that side of the body to be inclined inwardly and downwardly from the top edge when the body is in the normal position in order to discharge all of the contents of the body when tipped. The provision of doors on the side of the body presents a number of difficulties, such as maintaining the required strength in the doors and the body, and the difficulties that may be experienced in opening and closing the doors, particularly after a significant period of use when the doors and/or adjacent portion of the body may become distorted and accordingly present major difficulties in fitting and closing same.

In an attempt to avoid the problems associated with doors on the side of a tipping body, it has been proposed to incline the side wall of the body on the side to which it is tipped. This inclining of the side wall enables the body to be tilted to a less degree and still obtain discharge of the materials down the inclined wall when the body is in its maximum tipped position. This construction, however, has disadvantages in that the inclining of the side reduces the total carrying capacity of the body. Also it is necessary to effect a substantial extent of pivotal movement of the body so that the inclined side is sufficiently downwardly inclined during tipped for all of the contents to be discharged. This degree of pivotal movement can lead to instability in the vehicle during tipping due to the substantial degree of displacement of the centre of gravity of the body towards the tipping side.

SUMMARY OF THE INVENTION

It is an object of the present invention to provide a vehicle tipping system that provides improved safety and functional features, to substantially reduce the problem existing in current constructions.

In accordance with the present invention, there is provided a tipping vehicle comprising a chassis mounted on a plurality of wheels, a container body having an upper perimetrical frame and an open top elongated bowl made of flexible material and secured along the edge defining the open top to the perimetrical frame so the bowl is suspended therefrom to provide a generally semi-circular cross-section to the bowl, support means mounted on the chassis and operably coupled to the perimetrical frame to support the container body in a transport position with the perimetrical frame horizontal and a laterally tilted discharge position with the perimetrical frame inclined downwardly, and to move the perimetrical frame between said positions, and means to interact with the bowl when the perimetrical frame is in the discharge position to control the shape of the bowl so contents carried in the bowl will gravity discharge therefrom over the lower side of the perimetrical frame.

Preferably the means to interact with the bowl are arranged to deflect as the container body is moved into the discharge position, a marginal portion of the bowl extending the length of the lower side of the container body so that marginal portion forms a generally upwardly inclined surface extending a substantial distance upwardly from the lower side of the perimetrical frame. Also said means to interact with the bowl are arranged to deflect a marginal portion of the bowl extending the length of the upper side of the perimetrical frame upwardly with respect to the perimetrical frame as the container body is moved to the discharge position. This deflection applies a lifting force to the lower regions of the bowl to promote establishment of the upwardly inclined surface and increase in the upward extent thereof.

More specifically there is also provided a tipping vehicle comprising a chassis mounted on a plurality of wheels, a container body having an upper perimetrical frame and an open top elongated bowl made of flexible material and secured along the edge defining the open top to the perimetrical frame so the bowl is suspended therefrom to provide a generally semi-circular cross-section to the bowl, support means mounted on the chassis at each of two opposite ends of the container body, each support means being coupled to the perimetrical frame at the adjacent end of the container body so the container body is suspended between the two support means, each support means including tilt means operatively interposed between the support means and the adjacent end of the perimetrical frame, the tilt means being selectively actuated in unison to move the perimetrical frame between a horizontal transport position directly above the chassis and a downwardly inclined discharge position with the lower longitudinal side of the perimetrical frame disposed outwardly of the chassis, and guide means mounted on the chassis to deflect upwardly that marginal portion of the bowl adjacent the lower side of the perimetrical frame when the perimetrical frame is in said downwardly inclined position to provide a generally straight upwardly inclined portion of the bowl extending upwardly from said lower side of the perimetrical frame for a substantial distance from and for the length of the lower side of the perimetrical frame.

The body may be arranged to be tilted so one side or one end of the bowl is lowermost in the discharge position.

Preferably, means are provided to apply an increased tension to the material of the bowl in a direction to assist in the establishment of said upwardly inclined generally straight portion. The tensioning means are conveniently actuated in response to the moving of the perimetrical frame to said downwardly inclined discharge position.

The chassis may include a cradle providing load support to the lower part of the bowl when in the transport position. Conveniently, the cradle incorporates at the upper edge on the side to which the bowl is tipped a rail to form part of the guide means to deform the body as the body is lifted off the cradle and is tilted to the side over the rail. The rail deflects the wall of the bowl as the bowl is tipped to provide the downwardly inclined straight portion to direct the contents in the bowl over the lower edge of the perimetrical frame.

Alternatively, the guide means comprise two spaced parallel guide bars extending longitudinally of the chassis on the side thereof to which the container body is tilted in the discharge position, said guide bars being rigidly interconnected and pivotally mounted on the chassis to pivot together about a longitudinal axis relative to the chassis, said guide bars and the pivot axis thereof being relatively located so that as the container body is being tilted to the discharge position the guide bars engage the side of the bowl to deflect same to establish said upward inclination of the lower margin portion of the bowl from the lower side of the perimetrical frame. Conveniently, the perimetrical frame comprises two laterally spaced longitudinal beams and two cross members interconnecting the ends of the longitudinal beams to form a rectangular shaped frame. The respective ends of each longitudinal beam are pivotally connected to the respective cross members so each longitudinal beam can rotate about its longitudinal axis.

BRIEF DESCRIPTION OF THE DRAWINGS

The present invention will be more readily understood and appreciated in the following detailed description of the preferred embodiment with reference to the accompanying drawings.

DETAILED DESCRIPTION OF THE PREFERRED EMBODIMENTS

Figure 1:
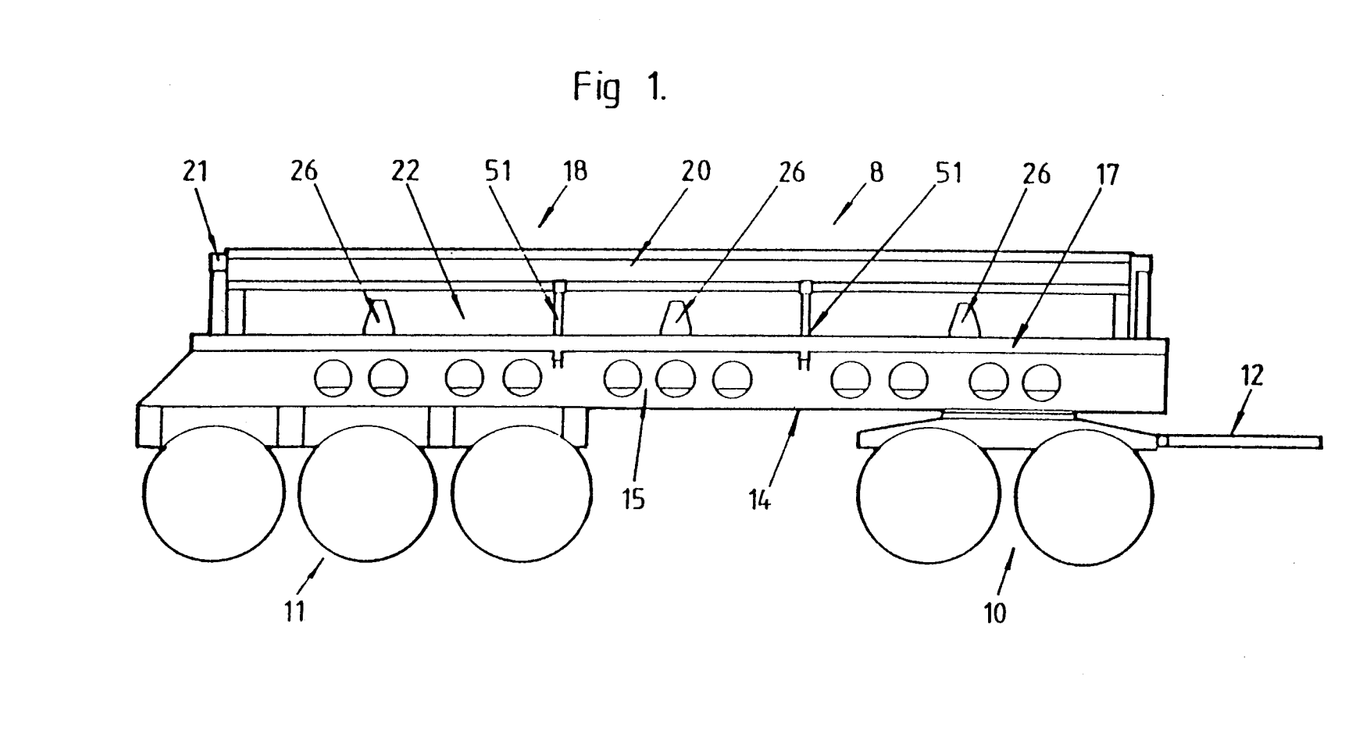
FIG. 1 is a side view of a road-trailer incorporating the preferred embodiment of the vehicle tipping system.

Referring now to FIG. 1, the vehicle shown is for road use, however, the vehicle may vary from small trailers, body trucks, or semi-trailers through to rail cars or heavy off-road vehicles, such as those used on mine sites. For the purpose of this description, the tipping system is fitted to a trailer, but this is not its only application.

The following description is made with reference to a side tipping system; nonetheless the present invention is applicable to a rear end tipping system. Thus references to "side", "tipping side", "end" and "rear end" may also be interpreted as "end", "rear end", "side" and "one/other side" respectively and consistently.

The tipping system is specifically adapted for vehicle mounted carrying and unloading systems for the handling of many types of loose bulk materials such as sand, soil, mineral ores, agricultural produce, chemical products and wastes in any situation where the material can be unloaded by gravity flow when the body is tipped.

As shown in FIG. 1, the vehicle 8 is a multi-wheeled trailer having a tandem forward wheel assembly 10 and a triple rear wheel assembly 11, and a tow bar indicated at 12 for connecting the tailer to a prime mover or another trailer. The chassis 14 of the vehicle comprises respective longitudinal structures 15 on either side of the vehicle and a plurality of transverse cradles 16 as seen more clearly in FIG. 5. The upper edge of each of the longitudinal structures 15 is in the form of a guide bar 17 of circular cross-section.

Figure 3:
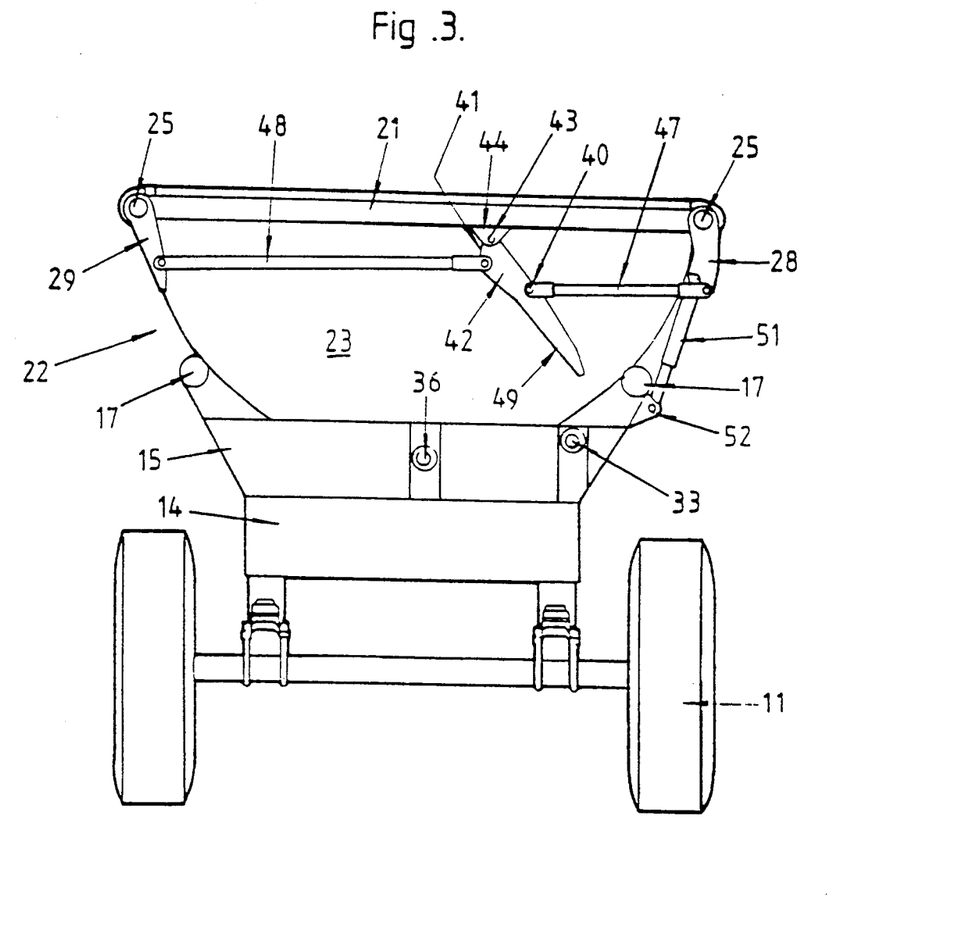
FIG. 3 is a view similar to FIG. 2 with the lifting cylinder and mechanism removed to show in more detail the cross linkage between the opposite sides of the bowl.

As seen in FIGS. 1 and 3 the container body which receives the material to be transported includes an upper perimetrical frame 18 having longitudinal coamings or beams 20 and end cross members 21 which will be described in more detail hereinafter. Suspended from the frame 18 is a bowl 22 of a generally semi-circular cross-section with closed ends 23. The respective upper edges of the bowl are secured such as by a plurality of bolts to the coamings 20 and cross members 21. The lower curved portion of the bowl 22 rests upon the complementary shaped upper face of the cradles 16 as seen in FIG. 5.

The bowl is made of a flexible material having suitable strength and wear resistant characteristics appropriate to the material being carried and is preferably of a high density polyethylene. The thickness of the material is also dependent upon the load to be carried, but will normally vary between 18 and 25 mm.

The material of the bowl 22 is flexible to the extent necessary to permit variation in the shape of the bowl, to facilitate unloading of the contents thereof, as previously discussed, however, the side walls and base are substantially non-stretchable under the loads the bowl is designed to carry. However, the material is resilient to the extent that it is not permanently dented or distorted by localised high loads that may arise during loading, transporting or discharging of materials of a non-uniform nature, such as rock or lump material.

Figure 5:
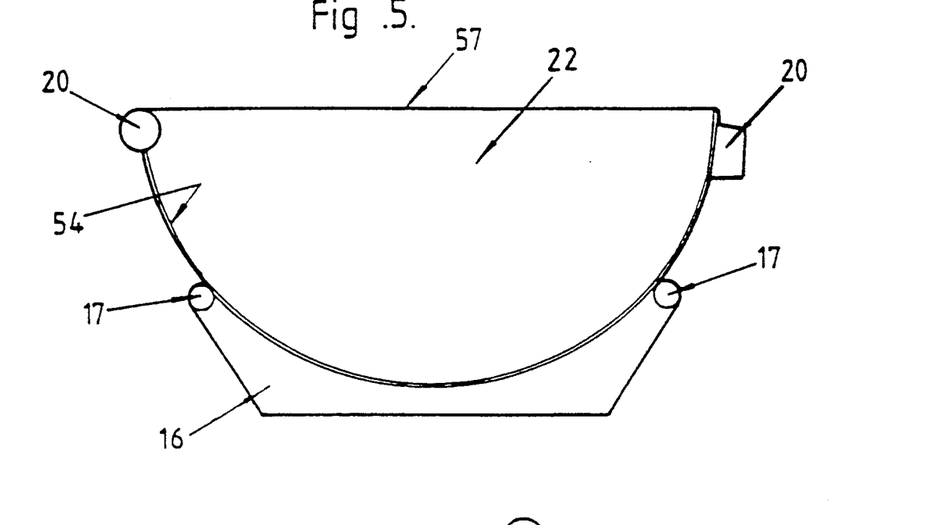
FIG. 5 is a diagrammatic cross-sectional view of the bowl in the transport position.
Figure 6:
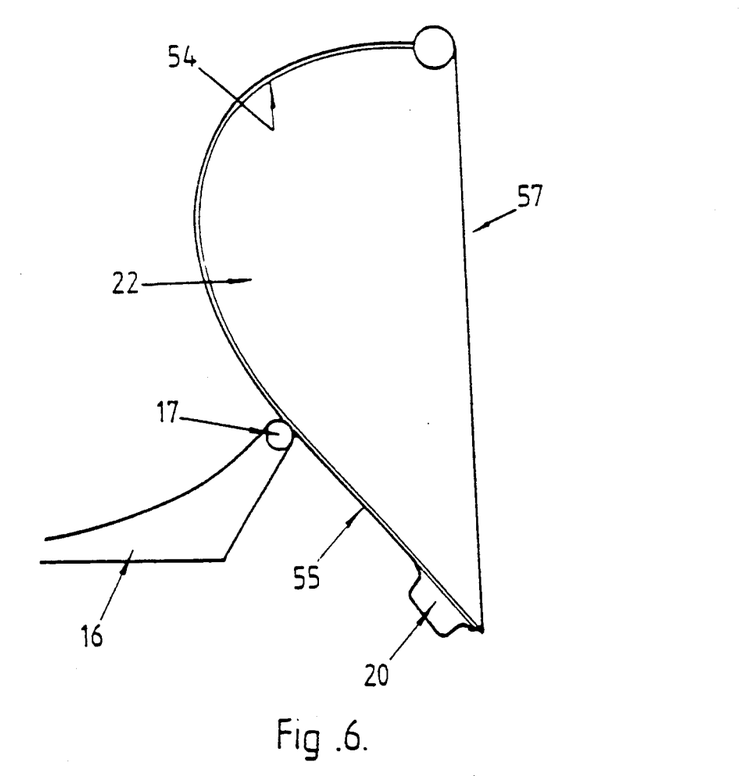
FIG. 6 is a view as in FIG. 5 with the bowl in the fully tipped position.

In view of the changes in the cross-sectional area of the bowl 22, as can be seen in FIGS. 5 and 6, the ends 23 of the bowl are made of a material having the required degree of stretchability and resilience to undergo such changes without folding or buckling of the bowl ends. The ends 23 are conveniently made of rubber of an appropriate quality.

In the embodiment shown, stiffening plates 26 are provided at spaced intervals along the length of the bowl 22 on the side of the bowl that is lowered during the tipping movement. These stiffening plates 26, being preferably made of spring steel, are shaped generally to the free shape of the wall of the bowl and are secured to the wall of the bowl to limit undesirable downward distortion of the contour of the flexible material of the wall during tipping. The stiffening plates 26 are positioned on the bowl to engage the bars 17 forming part of the longitudinal structure 15 during the tipping operation and to roll thereabout as hereinafter described.

The coaming beams 20 and cross members 21 are individually rigid, with each end of each coaming having a co-axial spigot 25 extending through the adjoining cross member 21 whereby the coaming 20 may rotate about the longitudinal axis thereof relative to the cross members. Each spigot 25 has an arm secured thereto, arms 28 being secured to the spigots on the coaming of the tipping side of the body and arms 29 on the spigots on the coaming on the opposite side, the lifting side.

Figure 2:
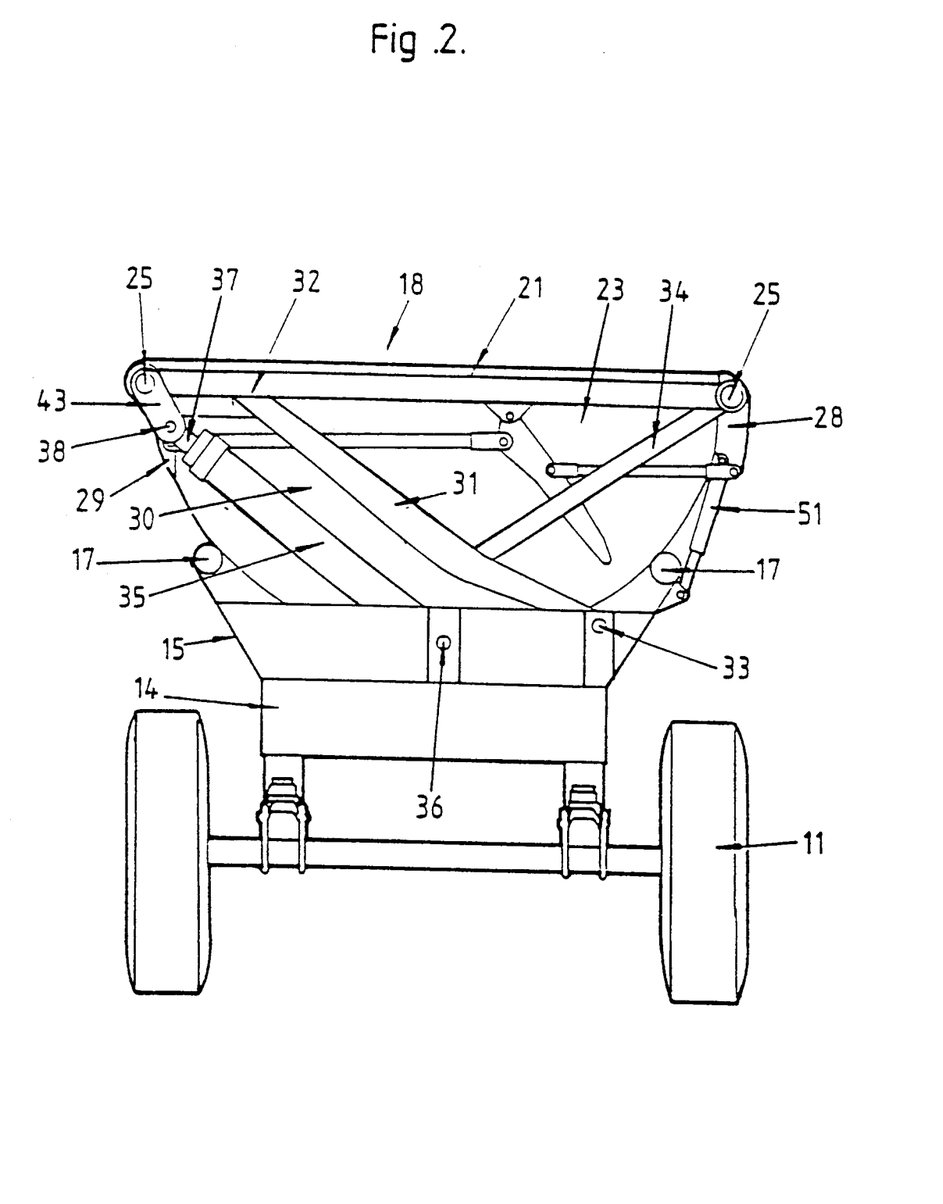
FIG. 2 is a rear end view of the vehicle of FIG. 1 with the bowl in the transport position.

The perimetrical frame 18 is supported at the respective ends thereof by front and rear tipping mechanisms 30 which are of identical construction. The following description, specifically relates to the rear tipping mechanism as illustrated in FIG. 2, applies equally to the front tipping mechanism at the opposite end of the body.

The lift bar 31 is rigidly attached to the cross member 21 at 32, and pivotally connected at 33 to the chassis 14. The brace member 34 is rigidly secured to the lift bar 31 and cross member 21 at its respective ends to increase the rigidity and strength of the structure formed by the cross member 21, lift bar 31 and brace member 34. The double acting hydraulic lift cylinder 35 is pivotally attached at its lower end to the chassis 14 at 36 with the piston rod 37 of the hydraulic cylinder 35 pivotally connected at 38 to the arm 43 rigidly attached to the spigot 25 of the coaming 20 on the lift side of the body.

The above described structure is operable to effect the tilting of the body by the extension of the hydraulic cylinder 35. As the piston rod 37 of the hydraulic cylinder 35 extends, the lift bar 31 will pivot with respect to the chassis about the pivot point 33 carrying with it the cross member 21 and the brace member 34. This will cause the coaming 20 on the tipping side of the body to be lowered and the coaming on the lifting side of the body to be raised. The tilting operation will be described in further detail hereinafter.

Associated with the tipping mechanism is a lever system to effect the limited degree of rotation of each of the longitudinal coamings 20 during the tipping operation. This system consists of a lever 42 pivotally connected at 43 to the bracket 44 secured on the cross member 21.

The arms 28 and 29 rigidly secured to the respective coamings 20 are pivotally connected to one end of respective links 47 and 48 the other ends of said links being pivotally connected to the lever 42 at 40 and 41, respectively. The extended end 49 of the lever 42 will engage the guide bar 17 on the tipping side of the vehicle as the body is being tilted by the extension of the hydraulic cylinder 35.

The coaming 20 extending along the length of the body on the tilting side thereof, is supported at intervals along its length by telescopic prop members 51, pivotally attached to the coaming 20 at the upper end and at the lower end to respective brackets 52 rigidly secured to the chassis 14. The prop members 51 have a fixed minimum length that is established when the body is in the non-tipping transport position and is extended as the body is moving to the tipping position. In the minimum length position the prop members 51 transfer part of the load on the coaming to the chassis.

The above described interconnection between the arms 28 and 29, and the connection of the arm 43 with the piston rod 37 of the hydraulic cylinder 35, results in the extending of the piston rod effecting tilting of the body relative to the chassis about pivot 33. The force applied to the arm 43 also applies a force to the arm 29 and through links 47 and 48 to the arm 28 and hence to the coaming on the tilt side of the body. Also there is provided a stiffening plate 54, secured along its upper edge to the coaming on the left side of the body, and projecting downwardly therefrom within the body to bear against the inner face of the flexible wall of the bowl 22. The stiffening plate 54 will thus rotate with the coaming thus preventing sagging of the flexible material of the bowl on the lift side thereof during the tilting of the body, and in fact deflecting that portion of the bowl outwardly as the bowl is tipped.

The actual tipping operation will now be described with reference to the tipping mechanism shown in FIG. 2, however, it is to be understood that the complementary tilting mechanism at the opposite end of the body will be operating simultaneously.

Figure 4:
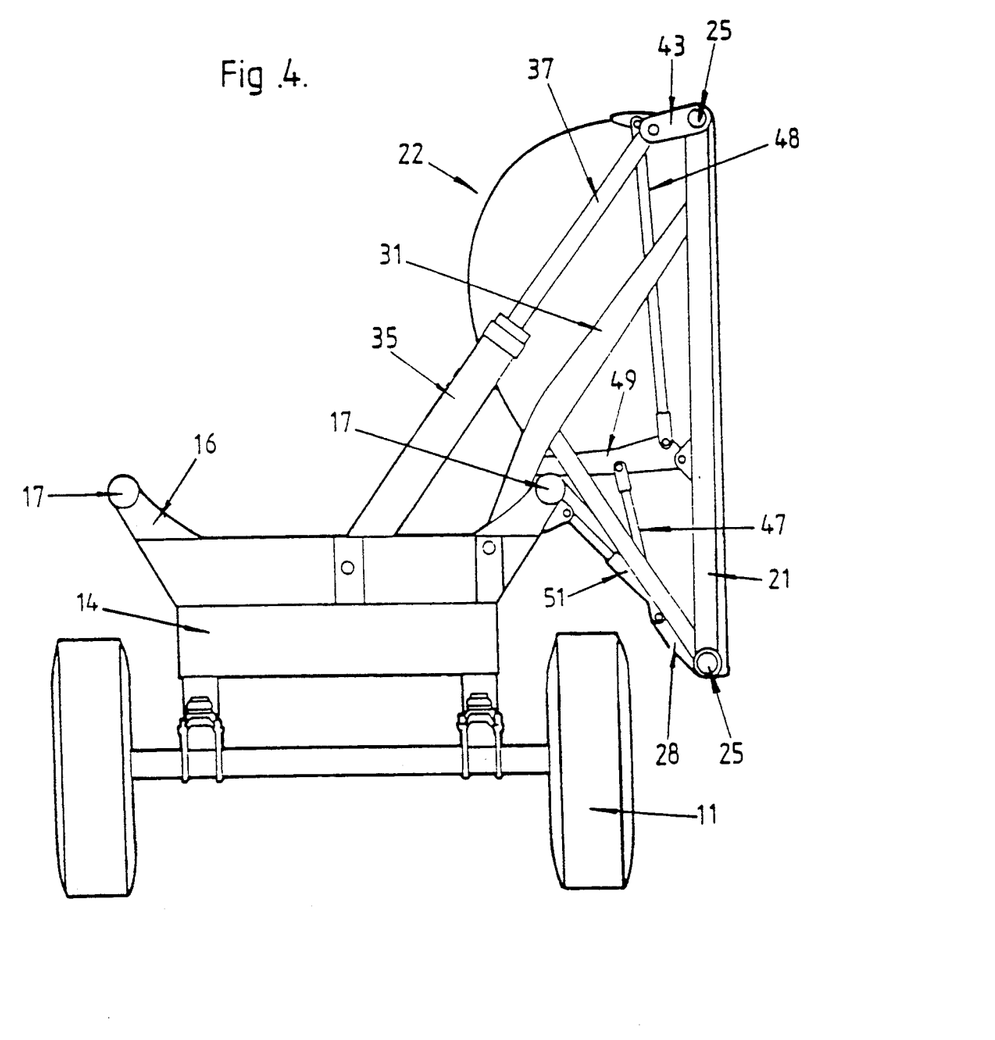
FIG. 4 is a view similar to that in FIG. 2 with the bowl in the tipping position.

Hydraulic fluid from an appropriate pump and through an appropriate control valve is provided to the hydraulic cylinder 35 so as to extend the piston rod 37. This will cause the lift bar 31 and brace member 34 to pivot about the axis 33 thereby causing the cross member 21 to tilt so as to lower the coaming on the tipping side of the vehicle and raise the coaming on the opposite lift side of the vehicle. As the piston rod 37 of the hydraulic cylinder 35 continues to extend, the above movement will progress until the coaming on the tipping side of the vehicle has been lowered and the coaming on the lift side of the vehicle has been raised sufficiently as shown in FIGS. 4 and 6 to cause the contents of the body to commence to discharge over the coaming on the tipping side of the vehicle. This discharging of the load will commence at some time before the hydraulic cylinder 35 is fully extended and the body has reached its fully tipped position as shown in FIGS. 4 and 6 of the drawings.

While the loaded bowl 22 is in the transport position with the frame 18 horizontal, the wall of the bowl will be seated on the cradle 16 and engage the guide bars 17 on each side of the chassis as seen in FIG. 5. During the tilting of the body the weight of the contents of the body will maintain the flexible wall of the body in contact with the guide bar 17 on the tipping side of the vehicle whilst it is lifted clear of the guide bar 17 on the lifting side of the vehicle. As the lifting movement continues, the coaming on the tipping side of the vehicle will be lowered and moved outwardly with respect to the chassis 14, thus causing the wall of the bowl 22 on the tipping side to pivot or roll about the guide bar 17, as the contents of the bowl also tend to move towards the tilting side of the bowl.

The contact maintained between the guide bar 17 and wall of the bowl on the tilting side thereof as the lifting side rises further prevents a downward deformation of the wall of the bowl on the tipping side as a result of the tendency of the contents of the bowl to move towards that side of the bowl. Also during this movement, the coaming on the lifting side of the bowl will pivot in the clockwise direction due to the extending of the hydraulic cylinder 35, and induce a similar clockwise rotating movement of the coaming on the tilting side of the bowl through the links 47 and 48. This results in an outward deflection of the wall of the bowl 22 by the rotation of the stiffening plate 54 on the lifting side of the bowl whilst at the same time the arm 28 on the tilting side of the bowl is drawn inwardly.

These movements and the resulting tensioning and reshaping of the wall of the bowl continue as the hydraulic cylinder is extended until the bowl reaches its final dumping position as shown in FIGS. 4 and 6. Upon reaching this position the lower portion 55 of the wall of the bowl between the guide bar 17 and the coaming on the tipping side of the bowl is substantially straight so that all of the material within the bowl will roll or slide down the straight inclined surface of the bowl to be discharged over the coaming on the tilting side of the bowl.

It will be appreciated that as the bowl takes up the position as shown in FIGS. 4 and 6, the actual load on the hydraulic cylinder will be reduced and hence the pressure therein will also reduce and thus there would be a tendency for the coaming 20 on the lift side to rotate in an anti-clockwise direction with respect to the cross member 21. This movement would tend to slacken the tension in the material of the bowl and could create a downward depression in the wall of the bowl in the tipping side between the coaming and the guide rail 17. To avoid this happening, and the possibility of material being trapped in that depression and not dumped from the bowl the downward extension 49 of the arm 42 as seen in FIG. 4 engages the guide bar 17 as the bowl is being tilted, thereby preventing anticlockwise rotation of the coamings and providing the necessary support to that portion of the bowl between the coaming and the guide bar 17 on the tipping side to maintain the wall in a generally downwardly inclined configuration as seen in FIG. 6.

Figure 7:
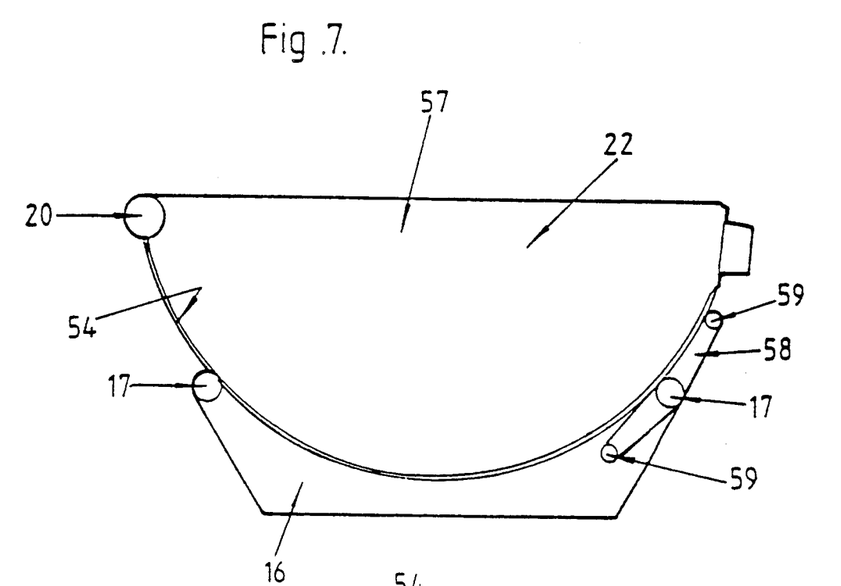
FIGS. 7 and 8 are views the same as in FIGS. 5 and 6 of a modified form of bowl support.
Figure 8:
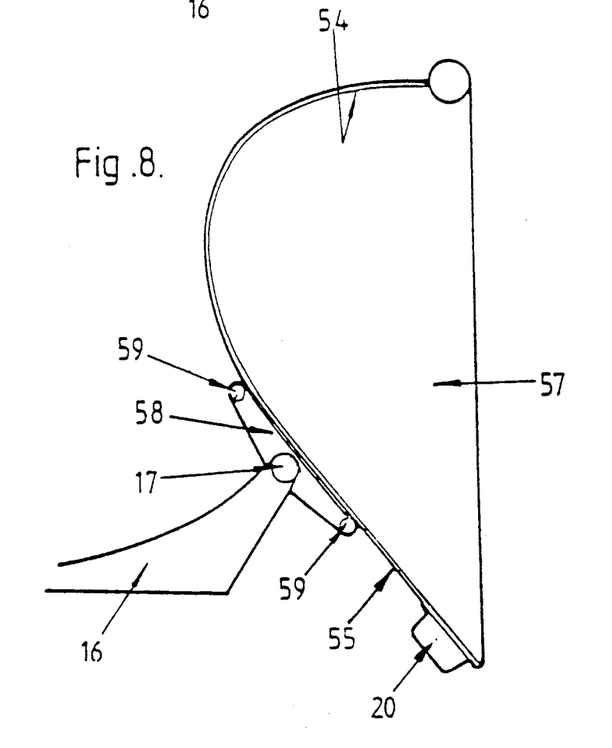

Referring now to FIGS. 7 and 8, there is shown therein diagrammatically a modification to the construction of the guide bar on the tipping side of the vehicle which will provide additional support to the lower portion of the bowl in the discharge position to maintain the downwardly inclined form of the lower portion of the bowl to promote the free passage of the material down and out of the bowl.

In this modified construction, a plurality of double ended arms 58 are mounted on the guide bar 17 so as to be rotatable thereon about the longitudinal axis of the guide bar 17. The arms 58 are distributed substantially evenly along the longitudianl length of the guide bars and are generally symmetrical with respect to the guide bar so that the arms project in a generally equal direction to either side thereof.

The arms are interconnected at each of their outer ends by respective secondary guide bars 59 which are rigidly secured to the arms 58 and extend the full longitudinal length of the bowl 22.

When the bowl is in the transport position as shown in FIG. 7, the arms 58 and secondary guide bars 59 do not provide significant support for the bowl 22 such support being basically provided by the cradle 16 and the coamings 20. As the bowl is being tipped to the discharge position, as shown in FIG. 8, the wall of the bowl on the tipping side comes into full contact with the secondary guide bars 59 and the arms 58 which rotate on the guide bar 17 as the tipping of the bowl progresses. As can be seen in FIG. 8, the lower portion of the bowl is supported over a significant length by the guide bar 17, secondary guide bars 59 and the arms 58, thereby enhancing the promotion of the discharge of the material from the bowl and preventing the formation of depressions wherein such material could be trapped and not effectively discharged.

It can be clearly seen in FIGS. 5 to 8 that the establishment of the substantially straight upwardly inclined lower marginal portion of the bowl in the discharge position is achieved primarily by the deformation of the cross-section of the bowl by the provision of the guide bar 17, and further assisted by the rotation of the coaming 20 on the lower side of the perimetrical frame and also by the rotation of the coaming on the upper side of the perimetrical frame together with the stiffening plate 54 attached thereto. This rotation is particularly evident by comparing the position of the respective coamings with relation to the line 57 in FIGS. 5 to 8 representing the upper edge of the bowl. Further in regard to the modified form of the guide rail as described with reference to FIGS. 7 and 8, where such a construction is used, the provision of the stiffening plates 26 may be avoided.

The claims defining the invention are as follows:

1. A tipping vehicle comprising a chassis mounted on a plurality of wheels:
 a container body having an upper perimetrical frame and an elongated bowl having an open top, the elongated bowl being made of flexible material and secured along the perimetrical edge defining the open top to the perimetrical frame so the bowl is suspended therefrom to provide a generally semi-circular cross-section to the bowl;
 support means mounted on the chassis and operably coupled to the perimetrical frame to support the container body in a transport position with the perimetrical frame horizontal and a laterally tilted discharge position with the perimetrical frame inclined downwardly, and to move the perimetrical frame between said positions; and
 means to interact with the bowl when the perimetrical frame is in the discharge position to control the shape of the bowl so contents carried in the bowl will gravity discharge therefrom over the lower side of the perimetrical frame.

2. A tipping vehicle as claimed in claim 1 wherein the means to interact with the bowl are arranged to deflect, as the container body is moved into the discharge position, a marginal portion of the bowl extending the length of the lower side of the container body so that said marginal portion forms a generally upwardly inclined surface extending a substantial distance upwardly from the lower side of the perimetrical frame.

3. A tipping vehicle as claimed in claim 2, wherein the means to interact with the bowl are arranged to deflect, as the container body is moved into the discharge position, a marginal portion of the bowl extending the length of the upper side of the perimetrical frame, upwardly with respect to the perimetrical frame to apply a lifting force to the lower regions of the bowl to promote establishment of the upwardly inclined surface and increase in the upward extent thereof.

4. A tipping vehicle as claimed in claim 3, wherein the perimetrical frame comprises two laterally spaced longitudinal beams and two cross members interconnecting the ends of the longitudinal beams to form a rectangular shaped frame, the respective ends of each longitudinal beam being pivotally connected to the respective cross members so each longitudinal beam can rotate about its longitudinal axis, said bowl having two parallel longitudinal edges secured to the respective longitudinal beams, and the means to interact with the bowl including means to effect angular movement of the longitudinal beams about the respective axes thereof in directions to deflect the respective marginal portions of the bowl upwardly as the container body moves from the transport position to the discharge position.

5. A tipping vehicle as claimed in claims 2, 3 or 4, wherein the means to interact with the marginal portion of the bowl adjacent the lower side of the perimetrical frame comprises guide means mounted on the chassis and extending substantially the length of the bowl intermediate the height thereof, the guide means presenting to the side of the bowl a surface positioned to engage the side of the bowl and about which the side of the bowl is deflected during the movement of the container body from the transport to the discharge position so that in the discharge position the lower marginal portion of the bowl is upwardly inclined from the lower side of the frame to at least the guide means.

6. A tipping vehicle as claimed in claim 5, wherein the guide means comprise two spaced parallel guide bars extending longitudinally of the chassis on the side thereof to which the container body is tilted to the discharge position, the guide bars being rigidly interconnected and pivotally mounted on the chassis to pivot together about a longitudinal axis relative to the chassis, the guide bars and the pivot axis thereof being relatively located so that as the container body is being tilted to the discharge position, the guide bars engage the side of the bowl to deflect same to establish said upward inclination of the lower portion of the bowl from the lower side of the frame.

7. A tipping vehicle comprising a chassis mounted on a plurality of wheels,
a container body having an upper perimetrical frame and an elongated bowl having an open top, the elongated bowl being made of flexible material and secured along the perimetrical edge defining the open top to the perimetrical frame so the bowl is suspended therefrom to provide a generally semicircular cross-section to the bowl;
support means mounted on the chassis at each of two opposite ends of the container body, each support means being coupled to the perimetrical frame at the adjacent end of the container body so the container body is suspended between the two support means;
each support means including tilt means operatively interposed between the support means and the adjacent end of the perimetal frame, the tilt means being selectively actuated in unison to move the perimetal frame between a horizontal transport position directly above the chassis and a downwardly inclined discharge position with the lower longitudinal side of the perimetal frame disposed outwardly of the chassis; and
guide means mounted on the chassis to deflect upwardly a marginal portion of the bowl adjacent the lower side of the perimetrical frame when the perimetrical frame is in said downwardly inclined position to provide a generally straight upwardly inclined portion of the bowl extending upwardly from said lower side of the perimetrical frame for a substantial distance from and for the length of the lower side of the perimetrical frame.

8. A tipping vehicle as claimed in claim 7, wherein means are provided to apply an increased tension to the material of the bowl in a direction to assist in the establishment of said upwardly inclined portion.

9. A tipping vehicle as claimed in claim 8, wherein the tensioning means are actuated in response to the moving of the perimetrical frame to said discharge position.

10. A tipping vehicle as claimed in any one of claims 7, 8, or 9, wherein the perimetrical frame comprises two laterally spaced longitudinal beams and two cross members interconnecting the ends of the longitudinal beams to form a rectangular shaped frame, the respective ends of each longitudinal beam being pivotally connected to the respective cross members so each longitudinal beam can rotate about its longitudinal axis.

11. A tipping vehicle as claimed in claim 10, wherein each support means includes a lift arm rigidly attached to the adjacent cross member and pivotally connected at a lower end to the chassis, and a selectively extendable member pivotally connected at the respective ends to the chassis and the perimetrical frame at respective locations spaced in the horizontal direction from the lift arm, the pivot axes of the lift arms and of the extendable members at the opposite ends of the perimetrical frame being respectively aligned, whereby extension of the extendable member at each end of the perimetrical frame, effects pivotal movement of the perimetrical frame about the axis of the pivotal connection of the lift arms to the chassis to tilt the perimetrical frame to the discharge position.

12. A tipping vehicle as claimed in claim 11, wherein the extendable member is operatively connected to said longitudinal beams of the perimetrical frame to effect angular movement of each said beams about the respective axes thereof in direction to deflect the respective marginal portions of the bowl upwardly as the perimetrical frame moves to the discharge position.

13. A tipping vehicle as claimed in claims 7, 8 or 9 wherein the guide means includes a plurality of parallel lift member extending longitudinally of the chassis and mounted thereon for pivotal movement about a longitudinal axis intermediate the lift members, said lift members being arranged to engage the bowl along the length thereof as the perimetrical frame is tilted to said downwardly inclined position and at respective locations individually spaced from the lower side of the perimetrical frame to effect upward deflection of the marginal portion of the bowl over a greater extent thereof.

14. A tipping vehicle as claimed in 1, wherein the means to interact with the bowl are arranged to deflect, as the container body is moved into the discharge position, a marginal portion of the bowl extending the length of the upper side of the perimetrical frame, upwardly with respect to the perimetrical frame to apply a lifting force to the lower regions of the bowl to promote establishment of a generally upwardly inclined surface extending a substantial distance upwardly from the lower side of the perimetrical frame, and increase in the upward extent thereof.

15. A tipping vehicle a claimed in claim 10, wherein the guide means includes a plurality of parallel lift members extending longitudinally of the chassis and mounted thereon for pivotal movement about a longitudinal axis intermediate the lift members, the lift members being arranged to engage the bowl along the length thereof as the perimetrical frame is tilted to the downwardly included position and at respective locations individually spaced from the lower side of the perimetrical frame to effect upward deflection of the marginal portion of the bowl over a greater extent thereof.

16. A tipping vehicle as claimed in claim 12, wherein the guide means includes a plurality of parallel lift members extending longitudinally of the chassis and mounted thereon for pivotal movement about a longitudinal axis intermediate the lift members, the lift members being arranged to engage the bowl along the length thereof as the perimetrical frame is tilted to the downwardly inclined position and at respective locations individually spaced from the lower side of the perimetrical frame to effect upward deflection of the marginal portion of the bowl over a greater extent thereof.

* * * * *

UNITED STATES PATENT AND TRADEMARK OFFICE
CERTIFICATE OF CORRECTION

PATENT NO. : 5,265,940

DATED : November 30, 1993

INVENTOR(S) : BERND OSTERMEYER

It is certified that error appears in the above-identified patent and that said Letters Patent is hereby corrected as shown below:

Col. 1, line 19, delete "ccentre", insert --centre--

Col. 7, line 44, delete "longitudianl", insert --longitudinal--

Col. 7, line 44, delete "guide bars", insert --guide bar--

Signed and Sealed this

Nineteenth Day of July, 1994

Attest:

BRUCE LEHMAN

Attesting Officer

Commissioner of Patents and Trademarks